US010543160B2

(12) United States Patent
Han et al.

(10) Patent No.: US 10,543,160 B2
(45) Date of Patent: Jan. 28, 2020

(54) COSMETIC COMPOSITION INCLUDING WATER SOLUBLE SCRUB PARTICLES CONTAINING POLYPEPTIDE AND/OR CELL CULTURE (71) Applicant: PAEAN AESTHETICS INC., Yuseong-gu Daejeon (KR)

(72) Inventors: Kyuboem Han, Yuseong-gu Daejeon (KR); Seong Soo Jeon, Gumjeong-gu Busan (KR); Jongcheon Ha, Yuseong-gu Daejeon (KR)

(73) Assignee: Paean Aesthetics Inc., Daejeon (KR)

( * ) Notice: Subject to any disclaimer, the term of this patent is extended or adjusted under 35 U.S.C. 154(b) by 0 days.

(21) Appl. No.: 15/768,675

(22) PCT Filed: Oct. 13, 2016

(86) PCT No.: PCT/KR2016/011468
§ 371 (c)(1),
(2) Date: Apr. 16, 2018

(87) PCT Pub. No.: WO2017/065508
PCT Pub. Date: Apr. 20, 2017

(65) Prior Publication Data
US 2018/0303739 A1 Oct. 25, 2018

(30) Foreign Application Priority Data
Oct. 15, 2015 (KR) .................. 10-2015-0144297

(51) Int. Cl.
*A61K 8/64* (2006.01)
*A61Q 19/00* (2006.01)
(Continued)

(52) U.S. Cl.
CPC .............. *A61K 8/64* (2013.01); *A61K 8/0241* (2013.01); *A61K 8/60* (2013.01); *A61K 8/735* (2013.01);
(Continued)

(58) Field of Classification Search
None
See application file for complete search history.

(56) References Cited

U.S. PATENT DOCUMENTS 6,162,447 A   12/2000  Fankhauser et al.
6,290,991 B1*  9/2001  Roser .................. A61K 9/0021
                                                424/502

(Continued)

FOREIGN PATENT DOCUMENTS

KR   1001638340000 B1   12/1998
KR   1020100098289   *  9/2010
(Continued)

OTHER PUBLICATIONS

International Search Report and Written Opinion for International application No. PCT/KR2016/011468, dated Feb. 17, 2017. English translation of International Search Report included.

*Primary Examiner* — Robert A Wax
*Assistant Examiner* — Melissa S Mercier
(74) *Attorney, Agent, or Firm* — Knobbe, Martens, Olson & Bear LLP (57) ABSTRACT The present invention relates to a non-aqueous cosmetic composition comprising water-soluble scrub particles containing a polypeptide or a cell culture component. More specifically, the present invention relates to a non-aqueous cosmetic composition comprising 0.01 wt % to 15 wt % of hard and angulated water-soluble scrub particles containing cell culture components or various polypeptides including a peptide and an oligopeptide. Further, the cosmetic compo- (Continued)

sition of the present invention provides a non-aqueous cosmetic composition which does not comprise active ingredients, but comprises water-soluble excipient scrub particles for maintaining or improving a scrubbing effect and adjusting viscosity or volume.

3 Claims, 6 Drawing Sheets

(51) Int. Cl.
    *A61K 8/02*     (2006.01)
    *A61K 8/60*     (2006.01)
    *A61K 8/73*     (2006.01)
    *A61K 8/98*     (2006.01)

(52) U.S. Cl.
    CPC .............. *A61K 8/981* (2013.01); *A61Q 19/00* (2013.01); *A61K 2800/28* (2013.01); *A61K 2800/412* (2013.01)

(56) References Cited

U.S. PATENT DOCUMENTS

| | | | |
|---|---|---|---|
| 6,351,433 B1 * | 2/2002 | Kosugi | ................ G11C 7/1039 |
| | | | 365/189.07 |
| 2014/0357544 A1 * | 12/2014 | Gonzales | ............. C11D 3/1253 |
| | | | 510/397 |
| 2015/0352345 A1 | 10/2015 | Sul et al. | |

FOREIGN PATENT DOCUMENTS

| | | |
|---|---|---|
| KR | 10-2012-0138180 A | 12/2012 |
| KR | 1020140009471 A | 7/2014 |
| KR | 10-2015-0066829 A | 6/2015 |

\* cited by examiner

COSMETIC COMPOSITION INCLUDING WATER SOLUBLE SCRUB PARTICLES CONTAINING POLYPEPTIDE AND/OR CELL CULTURE

CROSS-REFERENCE TO RELATED APPLICATIONS

This application is a U.S. national stage filing under 35 U.S.C. § 371 of International Application No. PCT/KR2016/011468 filed Oct. 13, 2016 entitled "Cosmetic Composition Including Water Soluble Scrub Particles Containing Polypeptide and/or Cell Culture," which claims priority to and benefit of Korean Application No. 10-2015-0144297 filed Oct. 15, 2015, entitled "Cosmetic Composition Including Water Soluble Scrub Particles Containing Polypeptide and/or Cell Culture." The contents of each of these applications are hereby incorporated herein by reference in their entireties.

TECHNICAL FIELD

The present invention relates to a cosmetic composition comprising water-soluble scrub particles containing a polypeptide and/or a cell culture component, and more specifically, to a cosmetic composition comprising 0.01 wt % to 15 wt % of hard and sharply angulated water-soluble scrub particles containing components included in a cell culture or a polymer in which a plurality of amino acids such as a polypeptide and an oligopeptide are condensed with respect to the total amount of the cosmetic composition.

BACKGROUND ART

Recently, according as an aging society has rapidly been progressed, antiaging cosmetics have been in the limelight, and bio cosmetics containing a growth factor or a stem cell culture medium have been developed.

As prior art associated with cosmetics containing the growth factor, Korean Patent Registration No. 10-0433373, Korean Patent Registration No. 10-1289062, Korean Patent Registration No. 10-2013-0024316, and the like have been disclosed to the public.

Further, prior art associated with cosmetics containing the stem cell culture medium includes Korean Patent Registration No. 10-1063299, Korean Patent Registration No. 10-1047873, Korean Patent Registration No. 10-2010-0098298, and the like.

However, a recombinant growth factor or growth factors included in the stem cell culture medium are proteins, and the proteins are instable according to physical or chemical environmental changes, and are easily hydrolyzed particularly in a state that water is present. Therefore, when the recombinant growth factor or the growth factors included in the stem cell culture medium is added to the cosmetic composition, it is not easy to maintain biological activities of the recombinant growth factor or the growth factors included in the stem cell culture medium.

In order to maintain activities of various peptides for a long time during a storage or distribution period or use time by protecting an amide bond of the easily hydrolysable proteins, methods of freeze-drying the proteins along with a composition comprising a polysaccharide such as mannitol and the like to promote the stabilization thereof, or methods of purifying the proteins to a high purity and adding an additive to the purified proteins of a liquid phase to stabilize biological activities of the proteins have been attempted. However, such technologies have not been easily applied to the cosmetics.

Particularly, an epidermal growth factor (hereinafter referred to as 'EGF'), rh-oligopeptide-1 or sh-oligopeptide-1, has a biological activity decrease since physical and chemical changes occur in a state that the epidermal growth factor not only is stored at room temperature, but also is kept refrigerated when storing the epidermal growth factor for a long time. Therefore, there are various problems in making the epidermal growth factor into a preparation for the commercialization in which the storage or distribution period is required.

European Patent Publication No. 205,051 discloses a composition comprising EGF, 1 to 10% of a surfactant, 5 to 45% of lipid, and 0.3 to 0.8% of a preservative as a cream composition for the skin and ophthalmology which is for preventing the activity decrease in the EGF.

European Patent Publication No. 267,015 and U.S. Pat. No. 4,717,717 disclose an EGF-containing stabilization composition in which a water-soluble cellulose polymer is added to the EGF. Further, European Patent Publication No. 398,619 discloses an EGF-containing stabilization composition in which cations of metals such as zinc and the like are added to the EGF.

Korean Patent Publication No. 10-1996-0013439 discloses a stable EGF composition containing one or more selected from the group consisting of phenol, polyethylene glycol, a fatty acid salt, a surfactant, sucrose, fatty acid ester, sodium sulfate, an amino acid, taurine, mannitol, gelatin, fibronectin, hyaluronic acid, and an organic acid buffer solution.

As other patents for stabilizing the EGF, Korean Patent Registration No. 10-0570358 discloses a nano vector composition containing the EGF and selenium, and cosmetics using the same, and Korean Patent Registration No. 10-0752990 discloses a composition for preventing or treating skin diseases comprising nanoliposome and a natural extract.

Although conventional technologies are used, it is not easy to maintain activities of the EGF in the cosmetics that are at a room temperature distribution condition, a non-sterile condition and an aqueous condition. Particularly, when the EGF is added to the cosmetics at a very low concentration level that is allowed in the cosmetics, it is almost impossible to maintain activities of the EGF during the period required in storage, distribution and use.

Further, it is difficult to obtain effects of the proteins since the proteins are not penetrated into the skin very well due to their large molecular weights although the proteins are added to the cosmetics. Therefore, methods of using a peptide convergence technology using protein transduction domain (PTD), applying a liposome technology of covering the growth factor with lipid to help skin penetration, or combining microneedle therapy system (MTS) are mainly used in bio cosmetics including the growth factor.

The present invention could stably maintain activities of the easily hydrolysable peptides for a long time by containing water-soluble scrub particles formed in the form of sharp and hard angulated particles comprising a polypeptide and/or a cell culture component in a non-aqueous cosmetic composition.

Further, the present invention has been completed by applying the non-aqueous cosmetic composition containing the water-soluble scrub particles onto the skin, and dissolving the scrub particles using an aqueous-based cosmetic including a skin emulsion, thereby confirming the fact that active ingredients of various peptide growth factors or cell culture contained in the scrub particles have an effect of being deeply penetrated into a cornified layer of the skin.

The term of peptide in the present specification means material in which two to hundreds of thousands of amino acids are condensation polymerized, and comprises a natural, recombinant or chemically synthesized polypeptide including all of dipeptide, tripeptide, and oligopeptide proteins and the like.

Further, the present inventor has completed the present invention by mixing water-soluble scrub particles which do not contain the active ingredients such as the polypeptide or cell culture together with the water-soluble scrub particles containing the active ingredients and adding the mixture to a non-aqueous cosmetic, thereby preparing a non-aqueous cosmetic composition which is capable of controlling the content of the water-soluble scrub particles containing the polypeptide and/or cell culture without decreasing a scrubbing effect.

DISCLOSURE

Technical Problem

A basic objective of the present invention is to provide a cosmetic composition comprising 0.01 wt % to 15 wt % of sharp and hard angulated water-soluble scrub particles containing a polypeptide.

Another objective of the present invention is to provide a cosmetic composition comprising 0.01 wt % to 15 wt % of sharp and hard angulated water-soluble scrub particles containing a cell culture component.

Another objective of the present invention is to provide a cosmetic composition comprising 0.01 wt % to 15 wt % of sharp and hard angulated water-soluble scrub particles containing both the polypeptide and the culture medium.

Another objective of the present invention is to provide a non-aqueous cosmetic composition comprising 0.01 wt % to 15 wt % of the sum of water-soluble scrub particles containing the foregoing polypeptide and/or a cell culture component, and water-soluble excipient scrub particles for extension or viscosity adjustment which do not contain the polypeptide or the cell culture component.

Technical Solution

The foregoing basic objective of the present invention may be achieved by providing a cosmetic composition comprising 0.01 wt % to 15 wt % of sharp and hard angulated water-soluble scrub particles containing the polypeptide.

The water-soluble scrub particles may contain 0.0001 wt % to 0.1 wt % of the polypeptide. The polypeptide of the present invention is material in which two to hundreds of thousands of the amino acids are condensation polymerized, and the number of the amino acids is usually in a range of two to hundreds of thousands, preferably in a range of 2 to 1,000, more preferably in a range of 2 to 100, and most preferably in a range of 2 to 80. Further, the water-soluble scrub particles are preferably formed in the form of hard and sharply angulated particles, and may have a particle size of 0.01 mm to 2 mm.

It is apprehended that a scrubbing effect may deteriorate when the particle size is less than 0.01 mm, and it is not preferable to use the water-soluble scrub particles on the skin since a feeling of irritation externally becomes severe when the particle size is 2 mm or more. More preferably, the scrub particles have a particle size of 0.1 mm to 1 mm.

The water-soluble scrub particles of the present invention containing the polypeptide may additionally include various types of peptide materials. The peptide used in the present invention may be growth factors, and may be the EGF among the growth factors.

Further, a cosmetic composition comprising the water-soluble scrub particles of the present invention containing the polypeptide may further comprise water-soluble scrub particles containing the polypeptide different from the water-soluble scrub particles of the present invention containing the polypeptide. Further, the cosmetic composition comprising the water-soluble scrub particles of the present invention containing the polypeptide may further comprise water-soluble scrub particles for extension or viscosity adjustment which do not contain the active ingredients such as the polypeptide and the cell culture component.

The non-aqueous cosmetic composition of the present invention comprising the water-soluble scrub particles containing the polypeptide and/or the cell culture component may be prepared in the formulation form of an essence, a cream or a lotion. The non-aqueous cosmetic composition of the present invention comprising the water-soluble scrub particles containing the polypeptide has excellent effects in wrinkle improvement and the like.

"Growth factors" in the present invention refer to peptides which are involved in differentiation and growth of cells. The growth factors, as proteins with relatively low molecular weights secreted by the cells for the purpose of mutual communication, perform various physiological functions, and a specific growth factor plays a role of promoting differentiation of a specific cell.

A growth factor used in the present invention may be an EGF. The EGF, as a strong cell differentiation promoting factor of various epithelial cells derived from an ectoderm and a mesoderm, is a peptide with a molecular weight of 6,200 Da which is widely distributed in the body fluid and has 53 amino acid residues.

The peptide EGF functions as a strong promoter for proliferation of epithelial cells, endothelial cells and fibroblasts, and promotes movements and proliferation of the epithelial cells during loss of the epithelial cells. Therefore, the peptide EGF has been used as a raw material for cosmetics by having an excellent wound healing effect and a wrinkle improving effect.

According to an embodiment of the present invention, the EGF may be an EGF which is prepared from a recombinant *E. coli* or a plant and is purified to a purity of 90% or more. The EGF shows an activity of one million international unit (IU) or more per mg when correcting measured activity values into an EGF standard product of United Kingdom's National Institute for Biological Standards and Control (NIBSC) in the measurement of activities using 3T3 fibroblasts.

The EGF is generally used in a small amount except for special cosmetics since a mixing limit of the EGF in the cosmetics is domestically regulated to 10 ppm (0.001 wt %), and the price of the EGF is relatively expensive. The peptide EGF mostly does not exhibit activities in cosmetics in which the peptide EGF has to be used in a very small amount due to its characteristics that are vulnerable to hydrolysis.

If it is assumed that the activities of the peptide EGF are maintained after the peptide EGF is added to the cosmetics, 100 IU of the EGF is contained in 1 g of the cosmetics although 0.1 mg (0.1 ppm) of the EGF is added to 1 kg of the cosmetics. Therefore, the peptide EGF may exhibit sufficient activities even when the peptide EGF is applied to the skin of the human body.

Therefore, in the present invention, water-soluble scrub particles containing 1 to 10,000 ppm (corresponding to 0.0001 to 1 wt %) of the peptide EGF were used, and wt % of a cosmetic composition comprising the water-soluble scrub particles containing the EGF of the above-mentioned concentration was adjusted between 0.01 wt % and 15 wt % such that a final peptide EGF content in the cosmetic composition always becomes 10 ppm or less.

Further, in order to prevent the scrubbing effect from being decreased when the water-soluble scrub particles containing the peptide EGF are less used, the water-soluble scrub particles which do not contain the active ingredients are added for the purpose of scrubbing effect maintenance, extension, and viscosity adjustment such that wt % of the total amount of the water-soluble scrub particles in the cosmetics becomes 15 wt % or less.

The water-soluble scrub particles in the present specification are preferably formed in the forms of hard and sharply angulated particles. The sharply angulated particles of the present invention may be formed in a polypyramid form. Further, the angulated scrub particles may be microneedles which are formed in the form of a tetrahedral or pyramid shaped microstructure.

Further, each face of the microneedles may be flat, may include irregularities, or may be hollow. Further, there may be defects including partial breakage in corners or apexes of the microneedles and the like. Additionally, a recessed portion may be formed on one or more faces of the microneedles, and the recessed portion may have a depth corresponding to no more than ½ of a height of the microneedles.

The foregoing other objective of the present invention may be achieved also by providing a non-aqueous cosmetic composition comprising 0.01 wt % to 15 wt % of the water-soluble scrub particles containing the cell culture component.

The water-soluble scrub particles may contain 0.0001 wt % to 10 wt % of a cell culture dried material. Moreover, the water-soluble scrub particles may be formed in the form of angulated sharp particles, and may have a particle size of 0.01 mm to 2 mm. It is apprehended that the scrubbing effect may be deteriorated when the particle size is less than 0.01 mm, and the feeling of irritation may become severe when the particle size is 2 mm or more. Therefore, the particle size of less than 0.01 mm and 2 mm or more is not preferable.

More preferably, the particle size is 0.1 mm to 1 mm.

The water-soluble scrub particles containing the cell culture dried material may additionally include peptides. The peptides may be growth factors, and may be the EGF among the growth factors.

Further, the non-aqueous cosmetic composition of the present invention comprising the water-soluble particles containing the cell culture dried material may further comprise the water-soluble scrub particles of the present invention containing the peptides. The peptides may be growth factors, and may be the EGF among the growth factors.

The non-aqueous cosmetic composition comprising the water-soluble scrub particles of the present invention containing the cell culture dried material may be prepared in the formulation of an essence, a cream or a lotion. The non-aqueous cosmetic composition comprising the water-soluble scrub particles of the present invention containing the cell culture dried material has effects in wrinkle improvement, whitening, and the like.

The non-aqueous cosmetic composition of the present invention comprising the water-soluble scrub particles containing a peptide or cell culture dried material may comprise an oil phase component containing 15 wt % to 25 wt % of higher alcohol, 40 wt % to 65 wt % of oil, 2 wt % to 3 wt % of wax, and 5 wt % to 20 wt % of tocopheryl acetate. The higher alcohol may be one or more selected from cetyl alcohol, cetostearyl alcohol, isostearyl alcohol and stearyl alcohol, or a combination thereof.

The oil may be a mixture of one or more selected from natural vegetable oils such as Jojoba oil, hydrogenated palm oil, avocado oil, olive oil, almond oil, macadamia nut oil, meadowfoam oil, palm oil, coconut oil, and castor oil.

In addition, the wax may be a synthetic wax, a microcrystalline wax, or a combination thereof.

It is easy to fill the hardness-adjusted cosmetic composition in a container by allowing the cosmetic composition of the present invention to comprise 85 wt % to 90 wt %, preferably 87 wt % to 88 wt % of the oil phase component containing higher alcohol, oil, wax, and tocopheryl acetate, thereby adjusting hardness of the cosmetic composition.

The non-aqueous cosmetic composition of the present invention comprising the water-soluble scrub particles of the present invention containing a peptide and/or a cell culture component comprises 0.5 wt % to 1.9 wt % of hyaluronic acid, 1.5 wt % to 10 wt % of monosaccharide, and 0.0001 wt % to 0.01 wt % of tromethamine. However, the non-aqueous cosmetic composition of the present invention may further comprise water-soluble scrub particles which do not contain the polypeptide or the cell culture component as particles for maintaining and improving the scrubbing effect or adjusting viscosity or volume.

The hyaluronic acid may be selected from sodium hyaluronate, hydrolyzed hyaluronic acid, and a combination thereof.

The monosaccharide may be selected from sorbitol, ascorbic acid, and a combination thereof.

Shaping scrub particles for maintaining or improving the scrubbing effect and adjusting viscosity or volume of the entire cosmetic composition, i.e., water-soluble scrub particles which do not contain the polypeptide or the cell culture component play roles of preventing excessive slippery of cosmetics and adjusting hardness of the cosmetics such that the cosmetics are suitably filled in the container.

Another objective of the present invention may be achieved by providing a non-aqueous cosmetic composition in which the water-soluble scrub particles for shaping, thickening or extension are additionally mixed with the scrub particles containing active ingredients of the present invention. Provided is a technical means which is capable of maintaining a scrub stimulating effect of a predetermined level on the skin although the water-soluble scrub particles containing the peptide or the cell culture component is reduced from a high wt % range to a low wt % range by additionally using the water-soluble scrub particles for extension.

Therefore, another objective of the present invention may be achieved by providing a non-aqueous cosmetic composition comprising 0.01 wt % to 15 wt % of a mixture of the water-soluble scrub particles containing the peptide or the cell culture component and the water-soluble scrub particles which do not contain the active ingredients.

The water-soluble scrub particles for extension may comprise hyaluronic acid or monosaccharide. The water-soluble scrub particles for extension of the present invention do not include water-soluble scrub particles for extension with a particle size of 2 mm or more. The water-soluble scrub particles for extension with the particle size of 2 mm or more are not preferable since a feeling of irritation becomes severe when the water-soluble scrub particles for extension have a particle size of 2 mm or more.

Figure 1:
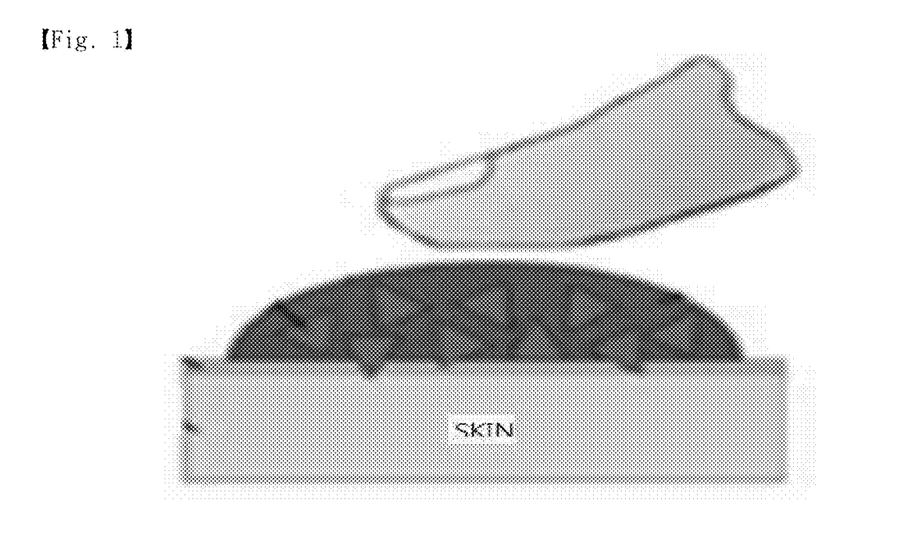
FIG. 1 is a conceptual diagram illustrating that a non-aqueous cosmetic composition of the present invention containing angulated shaped water-soluble scrub particles is applied to the skin.
Figure 6:
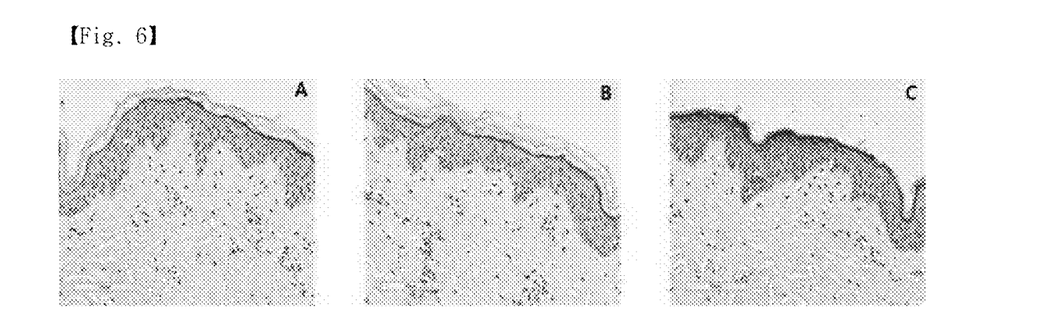
FIG. 6 is a photo obtained by scrubbing the skin of a pig with the non-aqueous cosmetic comprising water-soluble scrub particles containing the EGF that is a peptide, dyeing with an EGF antibody an extent that the EGF is penetrated into the pig skin, thereby photographing a cross-section of the EGF-penetrated pig skin.

The cornified layer of the skin is removed by applying the non-aqueous cosmetic composition comprising the water-soluble scrub particles containing the peptide or the cell culture dried material of the present invention on the skin, and patting or rubbing the non-aqueous cosmetic composition with the hand, thereby enabling apexes, corners or the like of the water-soluble scrub particles formed in a hard and angulated shape to apply a physical pressure to the skin (referring to FIG. 1 and FIG. 6). Subsequently, the applied angulated water-soluble scrub particles are dissolved using an aqueous-based cosmetic such as a skin emulsion such that active ingredients including a polypeptide or a cell culture component contained in the water-soluble scrub particles of the present invention are absorbed into the skin from which horny substance has been partially removed.

Advantageous Effects

A cosmetic composition of the present invention in which water-soluble scrub particles that contain the polypeptide and/or the cell culture components and are formed in hard and angulated particle shapes are included in the non-aqueous cosmetic can stably maintain activities of an easily hydrolysable peptide active ingredient or active ingredients contained in the cell culture at room temperature during the period of storage and distribution, or until the cosmetics are used.

Figure 7:
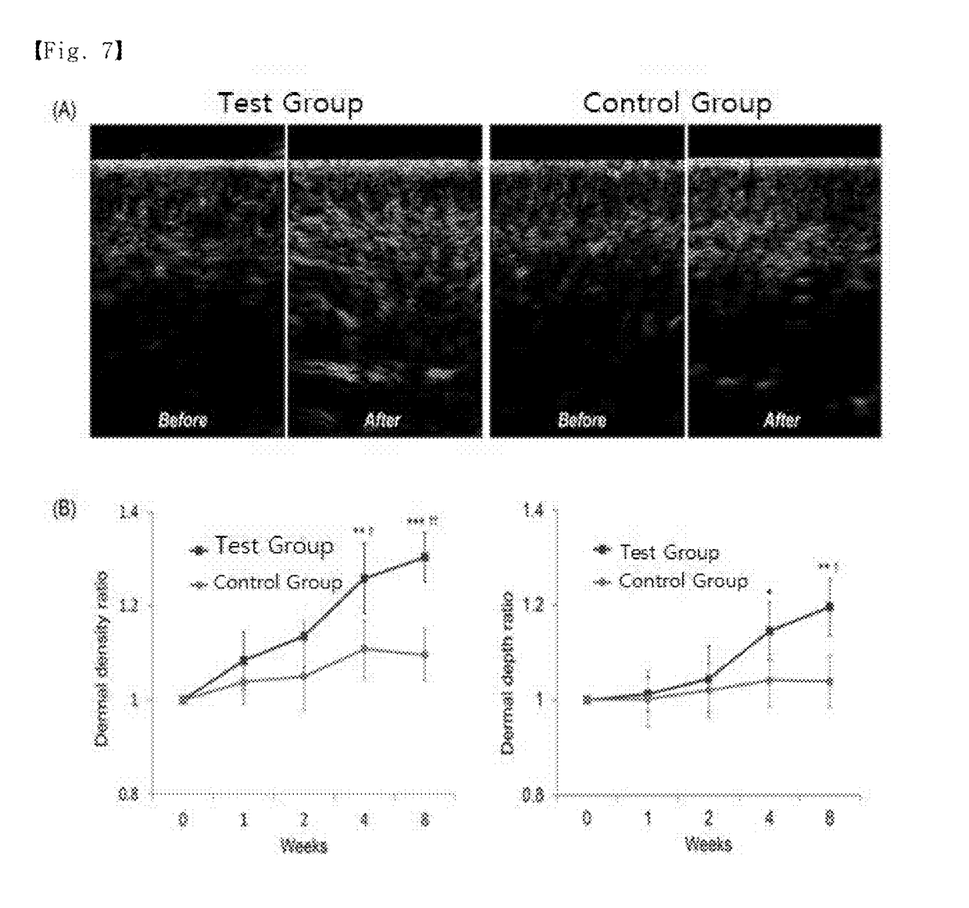
FIG. 7 shows results obtained by statistically processing and comparing effects for changes in skin thickness and density obtained by applying to the human body the non-aqueous cosmetic comprising the water-soluble scrub particles containing the EGF that is the peptide with those of a non-scrubbed control group.

Further, the water-soluble scrub particles according to the present invention are rubbed on the skin, there is an effect of partially removing a skin barrier such as horny substance (referring to FIG. 6). Therefore, when the water-soluble scrub particles are dissolved using the aqueous-based cosmetic including a skin emulsion after applying the non-aqueous cosmetic composition comprising the water-soluble scrub particles containing the active ingredients on the skin, the non-aqueous cosmetic composition exhibits an excellent skin improving effect by penetrating and delivering the active ingredients of the peptide growth factors or cell culture which are contained in the scrub particles of the present invention into the skin from which the cornified layer has been partially removed (referring to FIG. 7, FIG. 8, and FIG. 9).

MODE FOR INVENTION

Following Examples or accompanying drawings of the present invention will be described below in more detail. The present invention may, however, be embodied in different forms and should not be construed as limited to the Examples or drawings set forth herein. Rather, these Examples or drawings are provided so that this disclosure will be thorough and complete, and will fully convey the scope of the present invention to those skilled in the art.

Figure 2:
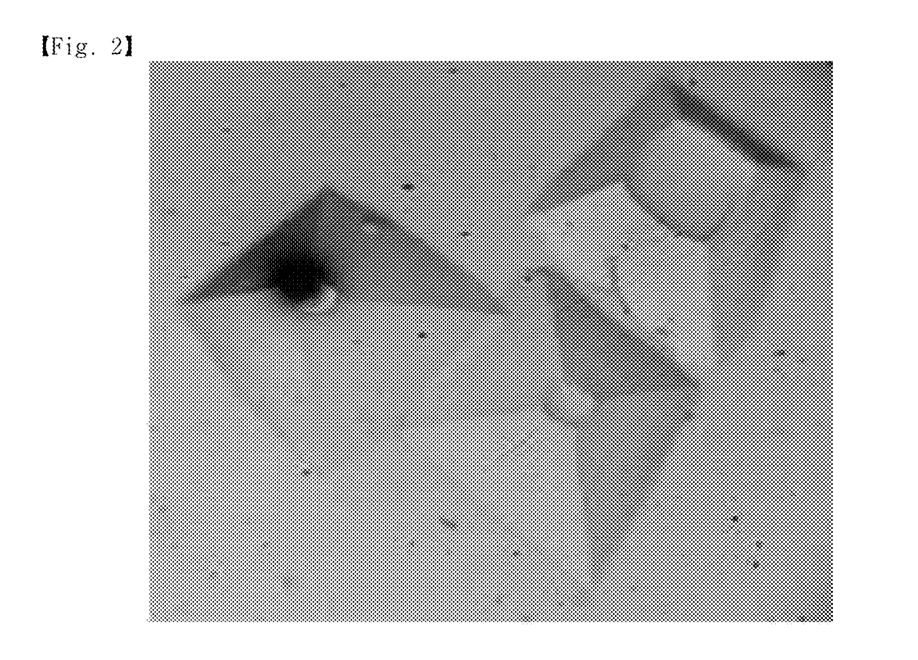
FIG. 2 is a photomicrograph illustrating angulated shaped water-soluble scrub particles with a particle size of 0.5 mm containing peptide growth factors prepared in Example 1 of the present invention.
Figure 3:
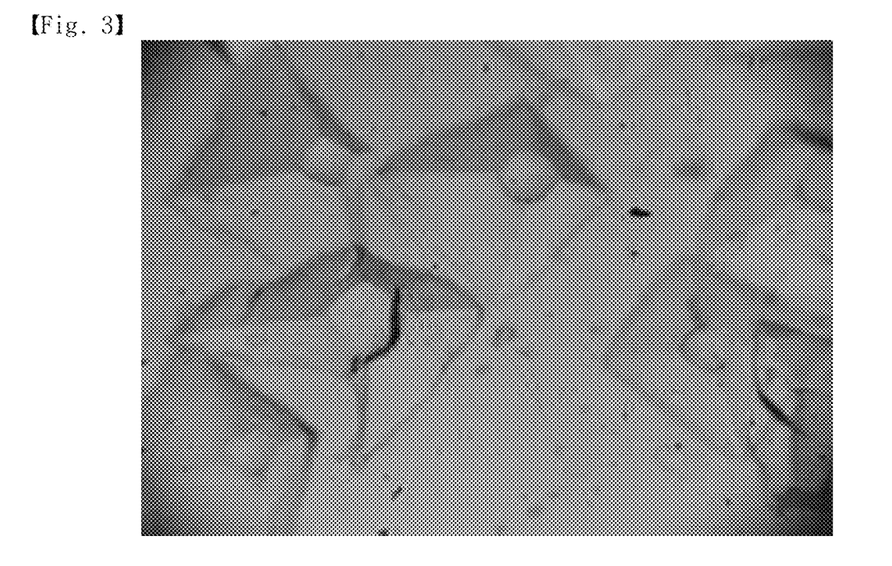
FIG. 3 is a photomicrograph for angulated shaped water-soluble scrub particles with a particle size of 0.3 mm containing cell culture dried material prepared in Example 1 of the present invention.
Figure 4:
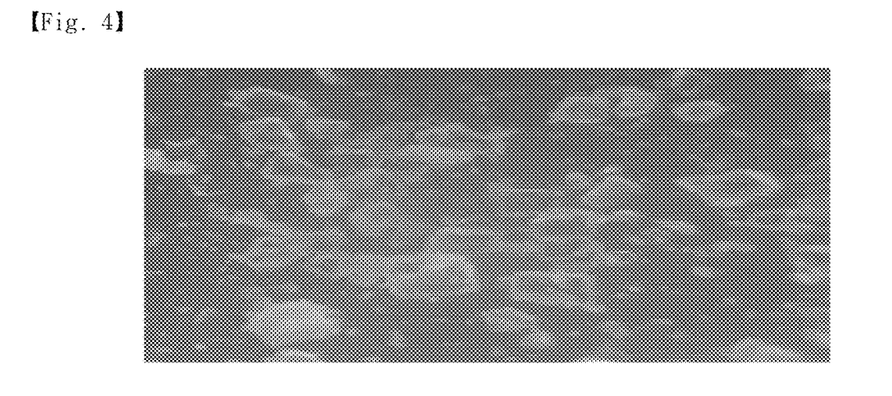
FIG. 4 is a photograph for water-soluble scrub particles for extension prepared in Example 6 of the present invention.
Figure 5:
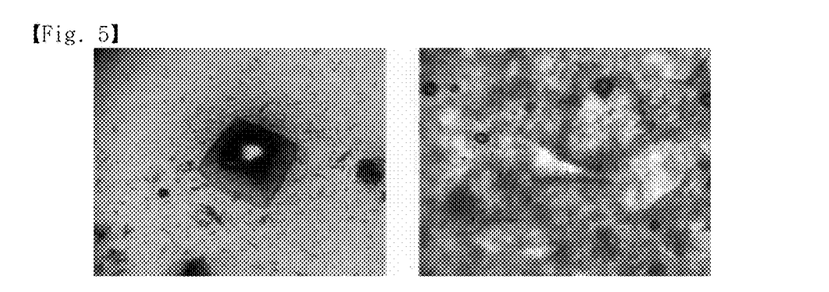
FIG. 5 is a photomicrograph for a non-aqueous cosmetic composition comprising the scrub particles for extension together with the water-soluble scrub particles containing the active ingredients of the present invention.

Example 1. Preparation of the Water-Soluble Scrub Particles Containing the EGF or the Cell Culture Component Sharply angulated shaped water-soluble scrub particles containing the EGF or the cell culture component were prepared by loading a mixed solution obtained by mixing 2 g of hyaluronic acid, 4 g of water and 200 ug of the EGF or a mixed solution obtained by mixing 2 g of hyaluronic acid and 4 g of the cell culture on a plate of which corners are formed in a sharply angulated pyramid shape, and in which small holes are formed, thereby drying the mixed solution loaded on the plate (referring to FIG. 2 or FIG. 3). The cell culture used in the present example, as a cell culture described in Korean Patent Laid-Open Publication No. 10-2010-0098298, contains a plurality of growth factors, and is used as a raw material for the cosmetics by having an excellent skin reproducing effect.

Examples 2 to 5

After respectively weighing oil phase components, water-soluble scrub particles containing active ingredients such as a polypeptide and/or a cell culture component, excipient scrub particles or components for thickening and extension, the weighed materials were slowly and uniformly mixed for about 5 hours in a stirrer in a state that the weighed materials were heated to 60° C. to prepare a mixture. A non-aqueous cosmetic composition comprising angulated water-soluble scrub particles of the present invention was prepared by cooling the mixture to 30° C. The non-aqueous cosmetic composition comprising the angulated water-soluble scrub particles prepared from a composition of Example 4 of Table 1 is formed in the form of an oil cream from which angulated particles with sharp ends are seen when observing the non-aqueous cosmetic composition by a microscope.

TABLE 1

|  |  |  | \multicolumn{4}{c}{Examples} |
| --- | --- | --- | --- | --- | --- | --- |
| Composition (wt %) | | | 2 | 3 | 4 | 5 |
| Oil phase components | Higher alcohol | Stearyl alcohol | 12 | 13 | 14 | 13 |
| | | Cetyl alcohol | 13 | 3 | 1 | 3 |
| | Oil | Jojoba oil | 20 | 0 | 55 | 30 |
| | | Olive oil | 20 | 55 | 0 | 35 |
| | Wax | Microcrystalline wax | 2 | 1 | 1 | 1 |
| | | Synthetic wax | 1 | 1 | 1 | 1 |
| | Tocopheryl acetate | | 20 | 15 | 15 | 15 |
| Active ingredient scrub particles (containing a peptide or a cell culture component) | | | 0.1 | 1 | 5 | 10 |
| Active ingredient-free excipient scrub particles | hyaluronic acid | Sodium hyaluronate | 1 | 1 | 1 | 0.5 |
| | | Hydrolyzed hyaluronic acid | 0.89 | 0 | 0 | 0 |
| | Monosaccharide | Sorbitol | 9.5 | 0.5 | 4.499 | 1 |
| | | Ascorbic acid | 0.5 | 9.499 | 0.5 | 0.49 |
| | | tromethamine | 0.01 | 0.001 | 0.001 | 0.01 |

Experimental Example 1. Evaluation of Skin Application/Skin Stimulation/Skin Flexibility After taking use tests on cosmetic compositions of Examples 2 to 5, test results were represented in Table 2. After performing a cleaning process on 10 women, samples of the Examples were evenly massaged on faces of the women, an aqueous-based skin emulsion was applied to the sample-massaged faces of the women, and then skin application, skin stimulation and skin flexibility were enabled to be evaluated on the aqueous-based skin emulsion applied faces of the women using a 5-point scale to obtain average values.

The 5-point scale is as follows:

1 point: very unsatisfactory 2 point: unsatisfactory 3 point: normal 4 point: satisfactory 5 point: very satisfactory

TABLE 2

| Evaluation items | Example 2 | Example 3 | Example 4 | Example 5 |
| --- | --- | --- | --- | --- |
| Skin application | 3.5 | 4.1 | 4.0 | 3.8 |
| Skin stimulation | 4.0 | 3.9 | 3.7 | 3.5 |
| Skin flexibility | 3.7 | 3.9 | 4.2 | 3.8 |

Referring to Table 2, all of the cosmetic compositions prepared in Examples 2 to 5 of the present invention exhibited high satisfaction values of normal or more in the respective items. Responses to the skin stimulation for angulated scrub particles exhibited different tendencies according to contents of the scrub particles.

Experimental Example 2. Evaluation of Stability Over Time

In order to evaluate stabilities over time of compositions prepared according to compositions of Examples 2 to 5, the compositions were each contained in an opaque plastic syringe container, the compositions contained in the opaque syringe containers were left alone at low temperature (4° C.), room temperature (25° C.) and high temperature (55° C.) for 3 months, contents were squeezed from the opaque syringe containers to evaluate stabilities over time on the contents, and results of the stabilities over time on the contents were represented in Table 2.

TABLE 3

| Temperature conditions | Example 2 | Example 3 | Example 4 | Example 5 |
| --- | --- | --- | --- | --- |
| Low temperature (4° C.) | No phase separation, confirmation of a scrub particle feeling, no color changes | No phase separation, maintenance of scrub particles, no color changes | No phase separation, maintenance of scrub particles, no color changes | No phase separation, maintenance of scrub particles, no color changes |
| Room temperature (25° C.) | No phase separation, confirmation of a scrub particle feeling, no color changes | No phase separation, maintenance of the scrub particles, no color changes | No phase separation, maintenance of scrub particles, no color changes | No phase separation, maintenance of scrub particles, no color changes |

TABLE 3-continued

| Temperature conditions | Example 2 | Example 3 | Example 4 | Example 5 |
|---|---|---|---|---|
| High temperature (55° C.) | No phase separation, decrease in the scrub particle feeling, change to yellow | No phase separation, maintenance of the scrub particles, change to yellow | No phase separation, maintenance of the scrub particles, change to pale yellow | Occurrence of a slight phase separation, maintenance of the scrub particles, change to pale yellow |

As shown in Table 3, although the cosmetic compositions of the present invention exhibited excellent stabilities over time, the cosmetic compositions of the present invention exhibited color changes caused by ascorbic acid at high temperature, and a slight phase separation occurred at high temperature in the composition of Example 5 comprising a large amount of the water-soluble scrub particles.

Experimental Example 3. Evaluation of Activity Stability

A process of evaluating activity stability of the EGF using a composition prepared according to compositions of Example 4 was performed. In order to evaluate the stability, the composition was contained in the opaque plastic syringe container, the composition contained in the opaque syringe container was left alone at room temperature (25° C.) and high temperature (55° C.) for 3 months, and activities of the EGF were specified from contents by the following method. A mixture obtained by putting angulated water-soluble scrub particles in the same amount as the composition of Example 4 into a skin emulsion that was the aqueous-based cosmetic was used as a test control group for activity measurement.

Experimental Materials

To measure cell proliferation activities for the EGF, a Balb/c 3T3 fibroblast cell line (ATCC #CCL-163) was used, a DMEM medium comprising 10% bovine serum was used as a culture medium for cell line passage, and a UltraMEM serum-free medium was used as a medium for analysis. United Kingdom's NIBSC purchased hEGF (Epidermal Growth Factor Human, rDNA derived, 91/530, 4000 IU/4 ug/mL) as an EGF activity measuring standard product to use hEGF in the measurement of EGF activities. An MTS reagent was used to measure cell proliferation caused by the EGF.

Method of Measuring Activities

After a three-month lapse since it was produced, weight of the cosmetic of the present invention was measured, the weight-measured cosmetic was put into the UltraMEM serum-free medium that was a culture medium for measuring activities of the EGF (the weight-measured cosmetic was controlled such that a final concentration of the EGF calculated from the content of the scrub particles became 1 ug/mL), the weight-measured cosmetic put into the UltraMEM serum-free medium was stirred very strongly to obtain an aqueous solution by centrifugation, and the aqueous solution was used in the activity analysis. After continuously diluting by two times an extract for activity measurement and an EGF activity standard product in 96-well plates such that the diluted extract for activity measurement and the EGF activity standard product were injected into each of the wells in an amount of 100 uL, $3 \times 10^3$ the Balb/c 3T3 fibroblasts were injected into each of the wells to obtain a mixture, and the mixture was cultivated in a 5% $CO_2$ culture medium at 37° C. for 72 hours. Thereafter, 40 uL of the MTS reagent was injected into each of the wells to obtain a mixture, the mixture was incubated in the 5% $CO_2$ culture medium at 37° C. for 4 hours, an absorbance of the incubated material was measured at 490 nm by a microreader, and values of the EGF standard product and extract were compared by parallel line assay using a PLA 2.0 program to calculate an EGF activity of the extract and calculate an EGF activity per 1 g of the cosmetic composition comprising the water-soluble scrub particles considering an extraction recovery ratio of 60%.

TABLE 4

| Temperature | Example 4 | Control group |
|---|---|---|
| Room temperature (25° C.) | $3.60 \times 10^3$ IU/g | 0 IU/g |
| High temperature (55° C.) | $2.05 \times 10^3$ IU/g | 0 IU/g |

As shown in Table 4, activities of the EGF were far more stable when the water-soluble scrub particles were added to the non-aqueous cosmetic composition of Example 4 than when the water-soluble scrub particles were added to the aqueous-based cosmetic (control group). At room temperature, the water-soluble scrub particles added to the non-aqueous cosmetic composition maintained activities of about 72% of $5.0 \times 10^3$ IU/g that was an average activity value of the initial EGF of the cosmetic composition of Example 4. Even at high temperature, the water-soluble scrub particles added to the non-aqueous cosmetic composition maintained activities of about 41%. Therefore, it could be seen that the cosmetic composition exhibited very excellent activity stability of the EGF.

Example 6. Preparation of Water-Soluble Scrub Particles for Extension

After thinly loading a mixed solution in which hyaluronic acid and water were mixed at a ratio of 1:2 on a flat plate or tray and drying the mixed solution loaded on the plate or tray, the dried mixed solution on the plate or tray was crushed to a particle size similar to that of angulated water-soluble scrub particles using a crusher. Thereafter, the crushed material was sieved by a mesh or sieve to obtain water-soluble excipient scrub particles for extension with a particle size of 2 mm or less which do not contain a peptide growth factor or cell culture dried material.

A dried mixed solution comprising ascorbic acid was crushed to a particle size similar to that of the angulated scrub particles using the crusher. The crushed material was sieved by a mesh or sieve to obtain water-soluble scrub particles for extension with a particle size of 2 mm or less which do not contain a polypeptide, a growth factor, or a cell culture.

Example 7. Preparation of Non-Aqueous Cosmetics

As represented in the following Table 5, components of all compositions except the angulated water-soluble scrub particles and the water-soluble excipient scrub particles for extension of the present invention containing active ingredients were prepared according to Example 4.

TABLE 5

| Compositions (wt %) | Examples | | | | |
|---|---|---|---|---|---|
| | 7 | 8 | 9 | 10 | 11 |
| Scrub particles containing active ingredients | 5 | 3.75 | 2.5 | 2.25 | 0 |
| Scrub particles for extension | 0 | 2.25 | 2.5 | 3.75 | 5 |

Experimental Example 1

Skin stimulation comparison tests according to a mixing ratio of the water-soluble scrub particles containing the active ingredients such as the polypeptide, the EGF, or the cell culture component and the water-soluble excipient scrub particles which do not contain the active ingredients were performed on cosmetic compositions of Examples 7 to 11, and the test results were represented in Table 6. The skin stimulation comparison tests were intended to evaluate, based on the judgement, a difference between skin stimulation values for cosmetics to which the water-soluble scrub particles containing the active ingredients and the water-soluble excipient scrub particles which do not contain the active ingredients were added. After performing a cleaning process on 10 women, samples of the Examples were evenly massaged on faces of the women, an aqueous-based skin emulsion was applied to the sample-massaged faces of the women, and then skin stimulation was enabled to be evaluated on the aqueous-based skin emulsion applied faces of the women using the 5-point scale to obtain average values.

The 5-point scale is as follows.
1 point: There is a very big difference
2 point: There is a difference
3 point: There is no saying
4 point: There is no difference
5 point: There is very little difference The evaluation process was performed by blind tests, skin stimulation values between the non-aqueous cosmetic comprising the water-soluble scrub particles containing the active ingredients as a control group and the non-aqueous cosmetic comprising the water-soluble excipient scrub particles which do not contain the active ingredients as a test group were compared.

TABLE 6

| Evaluation item | Examples 7 and 8 | Examples 7 and 9 | Examples 7 and 10 | Examples 7 and 11 |
|---|---|---|---|---|
| Skin stimulation | 4.2 | 4.2 | 4.2 | 4.1 |

As shown in Table 6, a result that a definite difference could not be distinguished between the skin stimulation values of the control group and the test group was obtained. Such a result shows that the present invention is capable of providing the non-aqueous cosmetic composition cosmetic composition comprising the water-soluble particles containing the peptide growth factor or the cell culture dried material with various concentrations without reducing an injection effect of the angulated water-soluble scrub particles containing the active ingredients by controlling wt % of the water-soluble excipient scrub particles which do not contain the active ingredients.

Example 12. Penetration Test of Pig Skin

Pig skin penetration test were performed on the test group and the control group by using the non-aqueous cosmetic comprising the water-soluble scrub particles of the present invention containing the EGF as the test group and using the EGF cosmetic which had the same contents and amount as the non-aqueous cosmetic, but did not use the water-soluble scrub particles as the control group, wherein the pig skin penetration tests were performed on the control group and the test group at the same compositions and conditions except that 60% of distilled water used in the control group was added to the test group such that the scrub particles were dissolved by the distilled water.

0.1 g of the test group was taken and coated on the surface of the pig skin, the test group coated on the pig skin surface was scrubbed, and 0.06 g of distilled water was added to melt scrub particles such that the melted scrub particles were additionally coated on the pig skin surface. 0.16 g of the control group (the EGF melted by adding distilled water) was taken and coated on the pig skin surface.

After coating a pig skin, the coated pig skin was cultured at 4° C. for 12 hours, the cultured pig skin was fixed using a 10% fixing solution such that a paraffin block is manufactured to make a segment with a thickness of 4 mm. After mounting a tissue on a slide, removing paraffin from the tissue, and passing the paraffin-removed tissue through a hydration process, a blocking process was performed on a segment of the tissue for 30 minutes. The tissue passing through the blocking process was treated with an anti-EGF anti-body to make the tissue react with the anti-EGF anti-body at 4° C. for 18 hours. The following day, the tissue reacted with the anti-EGF anti-body was washed with PBS, the tissue washed with PBS was treated with a second antibody to make the tissue react with the second antibody by a DAB reagent to obtain a reaction product, and the reaction product was observed by a microscope.

As shown in FIG. 6, an effect of removing horny substance by scrubbing of the test group (FIG. 6C) compared to the control group (FIG. 6B) could be confirmed. Further, an effect of the present invention enables scrubbing to penetrate the peptide growth factor EGF more deeply into a dermal part than the control group can be confirmed.

Example 13. Clinical Test

Clinical tests for skin wrinkle improvement were performed on 20 healthy male and female adults free from skin diseases, and more specifically, the clinical tests for wrinkle around eyes were performed on the 20 male and female adults. A control group was coated around left eyes of the subjects, and a test group was coated around right eyes of the subjects. The control group was obtained by adding 60% distilled water to the test group to melt the water-soluble scrub particles of the test group using the distilled water before using the control group. The clinical tests were conducted by coating respective samples on the skin around the eyes once every day, and observing and measuring the samples coated on the skin around the eyes for 8 weeks. In the case of the control group, 0.16 g of a control substance was coated on the cleaned application region for about 40 seconds after cleaning an application region. In the case of the test group, 0.1 g of a test substance was coated on the cleaned application region after cleaning the application region. After coating the control and test substances on the application regions, the control and test substances coated on the application regions were scrubbed for about 20 seconds, about 60 uL of distilled water was added to the scrubbed control and test substances on the application regions, and the scrubbed control and test substances on the application regions were additionally scrubbed for about 20 seconds using the distilled water. The measurement process was performed by observing and measuring the control and test substances on the application regions for 1 week, 2 weeks, 3 weeks, 4 weeks, and 8 weeks after coating the test substance.

A-one pro face diagnostic equipment, Ultrascan UC22 skin ultrasonic equipment, investigator global assessment (IGA), and patient global assessment (PGA) were used as clinical evaluation indicators. The IGA was digitized by scoring the extent of wrinkles through visual evaluation of two dermatologists based on wrinkle severity rating scale (WSRS) as a 5-point scale. The PGA was represented by digitizing satisfaction of the subjects into values through a 4-point scale.

Figure 8:
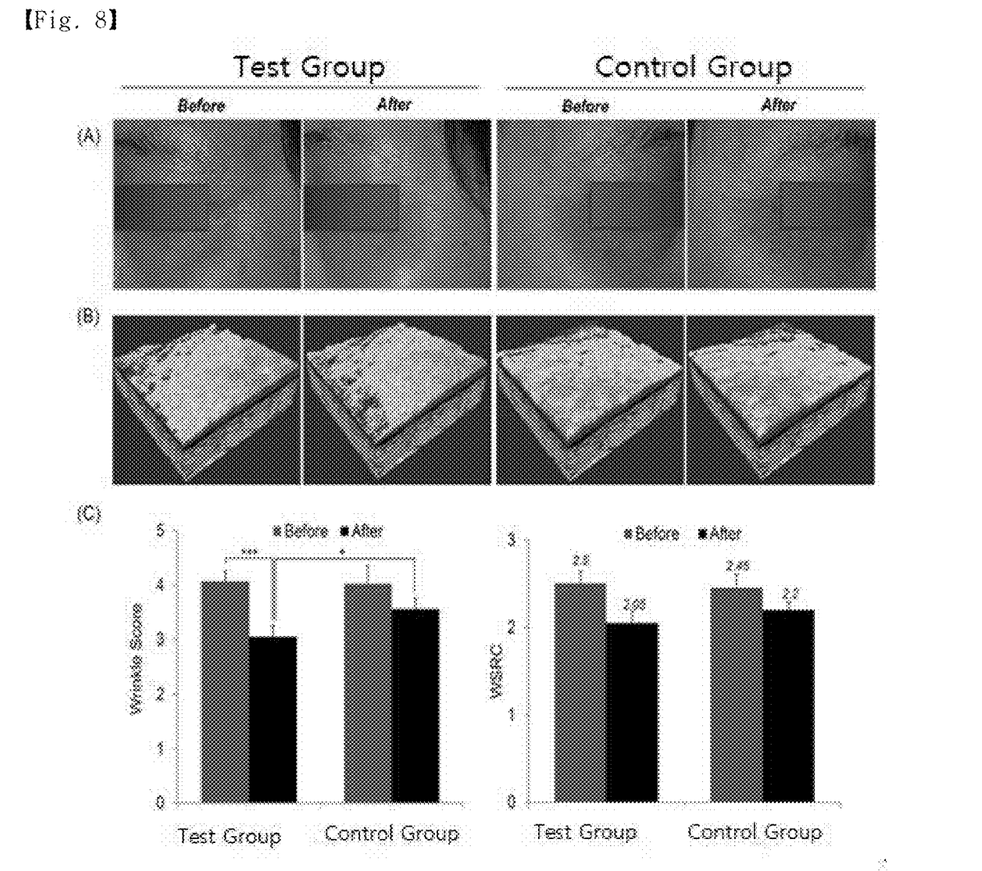
FIG. 8 shows results obtained by statistically processing and comparing wrinkle improving effects obtained by applying to the human body the non-aqueous cosmetic comprising the water-soluble scrub particles containing the EGF that is the peptide with those of a non-scrubbed control group.
Figure 9:
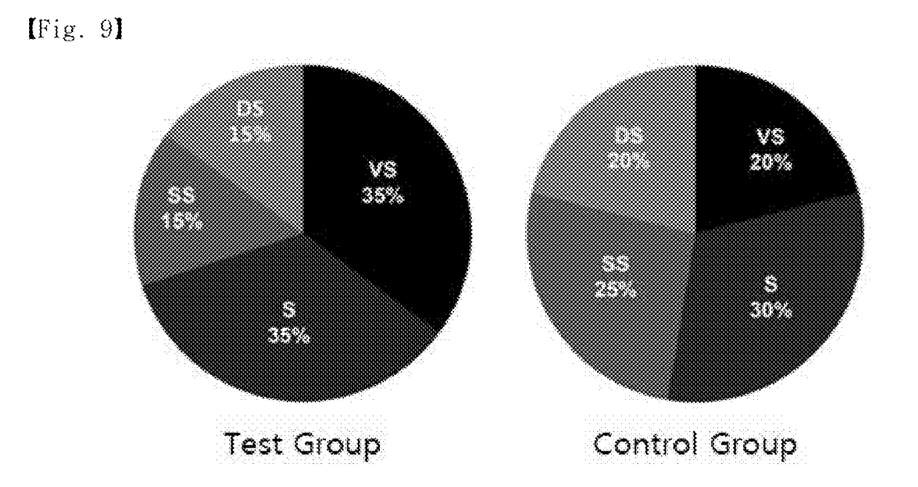
FIG. 9 is a result of evaluating levels of satisfaction of 20 subjects by applying to the human body the non-aqueous cosmetic comprising the water-soluble scrub particles containing the EGF that is the peptide.

As results of the clinical tests, it is confirmed that thickness and density of a skin dermis were increased in the test group compared to the control group (refer to FIG. 7), and an effect of improving wrinkles of the skin by scrubbing of the peptide EGF-containing particles was confirmed (refer to FIG. 8). Further, it was confirmed from satisfaction survey results of the subjects that the subjects shown less aversion about scrubbing by exhibiting a high satisfaction extent of 70% for the test group compared to a satisfaction extent of 50% for the control group (refer to FIG. 9).

The invention claimed is:

1. A cosmetic composition comprising:
   an oil phase in an amount ranged between 85 wt % and 90 wt % with reference to a total weight of the cosmetic composition; and
   angulated water-soluble scrub particles having a particle size of 0.01 mm to 2 mm and being in an amount ranged between 0.01 wt % and 15 wt % with reference to the total weight of the cosmetic composition,
   wherein the angulated water-soluble scrub particles comprise first particles and second particles,
   wherein the first particles comprise a water-soluble material and at least one polypeptide such that, when in contact with water, the water-soluble material dissolves and the at least one polypeptide is released, whereas the second particles comprise a water-soluble material but does not comprise a polypeptide.

2. The cosmetic composition of claim 1, wherein the first particles of the angulated water-soluble scrub particles contain at least one polypeptide in an amount ranged between 0.001 wt % and 1 wt % with reference to the total weight of the cosmetic composition.

3. The cosmetic composition of claim 1, wherein the water-soluble material comprises at least one selected from the group consisting of hyaluronic acid and monosaccharide.

* * * * *